(12) United States Patent
Kikuchi et al.

(10) Patent No.: US 7,616,292 B2
(45) Date of Patent: Nov. 10, 2009

(54) EXAMINATION APPARATUS

(75) Inventors: Susumu Kikuchi, Hachioji (JP);
Yoshihiro Kawano, Fuchu (JP);
Masahiro Oba, Fuchu (JP)

(73) Assignee: Olympus Corporation, Tokyo (JP)

( * ) Notice: Subject to any disclaimer, the term of this patent is extended or adjusted under 35 U.S.C. 154(b) by 251 days.

(21) Appl. No.: 11/648,638

(22) Filed: Jan. 3, 2007

(65) Prior Publication Data

US 2007/0247523 A1 Oct. 25, 2007

(30) Foreign Application Priority Data

Jan. 6, 2006 (JP) ............................. 2006-001670

(51) Int. Cl.
*G01C 11/12* (2006.01)
(52) U.S. Cl. ........................................ 356/2
(58) Field of Classification Search ............. 356/2, 356/601–613, 625–640
See application file for complete search history.

(56) References Cited

U.S. PATENT DOCUMENTS

| | | | |
|---|---|---|---|
| 6,160,908 A * | 12/2000 | Hakozaki | .................... 382/154 |
| 6,169,289 B1 | 1/2001 | White et al. | |
| 7,180,661 B2 * | 2/2007 | Sasaki | ........................ 359/385 |
| 2004/0021771 A1 | 2/2004 | Stearns et al. | |
| 2005/0187441 A1 * | 8/2005 | Kawasaki et al. | ............. 600/315 |
| 2006/0109546 A1 * | 5/2006 | Namba et al. | ................ 359/385 |

FOREIGN PATENT DOCUMENTS

| WO | 00/71028 A1 | 11/2000 |
|---|---|---|
| WO | 2004/008123 A1 | 1/2004 |

OTHER PUBLICATIONS

Susumu Kikuchi et al., "Three-dimensional image reconstruction for biological micro-specimens using a double-axis fluorescence microscope," Optics Communications, pp. 21-26 (1997).

Susumu Kikuchi et al., "Three-dimensional microscope computed tomography based on generalized Radon transform for optical imaging systems," Optics Communications, pp. 725-733 (1996).

* cited by examiner

*Primary Examiner*—Michael P Stafira
(74) *Attorney, Agent, or Firm*—Pillsbury Winthrop Shaw Pittman, LLP

(57) ABSTRACT

The invention provides an examination apparatus including an objective optical system for positioning a focal point inside a specimen mounted on a stage; an image-acquisition apparatus for detecting light emitted in different optical-axis directions from the vicinity of the focal point inside the specimen and collected by the objective optical system to acquire a plurality of pieces of image information; and a three-dimensional image forming unit for forming a three-dimensional image of a light-emitting site in the vicinity of the focal point based on the plurality of pieces of image information acquired by the image-acquiring apparatus.

5 Claims, 15 Drawing Sheets

EXAMINATION APPARATUS

BACKGROUND OF THE INVENTION

1. Field of the Invention

The present invention relates to an examination apparatus for acquiring three-dimensional images of a specimen.

This application is based on Japanese Patent Application No. 2006-001670, the content of which is incorporated herein by reference.

2. Description of Related Art

In a known technology in the related art, light-emitting areas, in which light is emitted from light-emitting points located inside a specimen such as a small laboratory animal and appears on the surface of the specimen, form a surface image, which is imaged from a plurality of directions, and the light-emitting areas on the surface of the specimen, which is represented three-dimensionally, are superimposed to be three-dimensionally displayed (for example, see US Patent Application No. 2004/0021771 (hereinafter referred to as Document 1)).

However, with the technology in Document 1, it is not possible to observe an image of the light-emitting sites inside the specimen.

A known apparatus for observing an image of the light-emitting sites inside a specimen is a confocal fluorescence microscope. Because a confocal fluorescence microscope images only light passing through a confocal pinhole, which is located at a conjugate position with respect to a focal point of an objective lens, it is possible to acquire an image of the light-emitting sites inside the specimen with extremely high resolution in the optical-axis direction. Then, based on a plurality of images acquired by shifting the focal point in the optical-axis direction, it is possible, in principle, to form a three-dimensional image of the light-emitting sites inside the specimen.

In practice, however, because the specimen, such as a small laboratory animal, is formed of scattering substances, the light emitted from the light-emitting sites located deep within the specimen is scattered before it reaches the specimen surface. Therefore, when observing sites deep inside the specimen, such as a small laboratory animal, from outside using a confocal fluorescence microscope apparatus, the light from the light-emitting sites is scattered, which causes the amount of light passing through the confocal pinhole to be reduced. This causes a problem in that, in some cases, it is almost impossible to form an image.

Conversely, when the pinhole diameter is increased, because the depth of field is increased, it is possible to make a lot of the light from the vicinity of the light-emitting sites inside the specimen pass through the pinhole, and it is thus possible to acquire a bright image.

However, when the depth of field is increased, an image which is in-focus at the focal point and focus-shifted images at positions shifted towards both sides in the optical-axis direction of the focal point are superimposed and acquired by an image-acquisition device, and it is thus not possible to acquire a clear image. Therefore, even though a plurality of unclear images acquired by shifting the focal position in the optical-axis direction are used, there is a problem in that it is not possible to acquire a clear three-dimensional image.

BRIEF SUMMARY OF THE INVENTION

An object of this invention is to provide an examination apparatus which can acquire clear three-dimensional images of light-emitting sites inside a specimen.

The present invention provides an examination apparatus comprising an objective optical system for positioning a focal point inside a specimen mounted on a stage; an image-acquisition apparatus for detecting light emitted in different optical-axis directions from the vicinity of the focal point inside the specimen and collected by the objective optical system to acquire a plurality of pieces of image information; and a three-dimensional image forming unit for forming a three-dimensional image of a light-emitting site in the vicinity of the focal point based on the plurality of pieces of image information acquired by the image-acquisition apparatus.

With this examination apparatus, the focal point of the objective optical system is located at the light-emitting site inside the specimen, and by operating the image-acquisition apparatus, the light emitted from the vicinity of the focal point is collected by the objective optical system, and a plurality of pieces of image information formed by imaging the vicinity of the focal point from a plurality of different directions are acquired. Then, based on the plurality of pieces of image information acquired, by operating the three-dimensional image forming unit, a three-dimensional image of the light-emitting site in the vicinity of the focal point is formed.

In this case, the image acquired in each optical-axis direction by an optical system having a depth of field deeper than that in confocal observation is unclear because an image at the focal position and images shifted in the optical-axis direction from the focal position are overlapped and acquired. However, in the vicinity of the focal position, it includes image information having a high resolution in a direction orthogonal to the optical axis. Therefore, it is possible to acquire a clear three-dimensional image by eliminating the unclear images.

Thus, according to the examination apparatus described above, by using a plurality of pieces of image information formed by imaging the light-emitting site in the vicinity of the focal point from different optical-axis directions, it is possible to acquire a clear three-dimensional image of the light-emitting site in the vicinity of the focal point.

In the examination apparatus described above, the image-acquisition apparatus may include a rotation apparatus for relatively rotating the specimen and the objective optical system about an axis intersecting the optical axis in the vicinity of the focal point.

With this configuration, by operating the rotation apparatus to relatively rotate the specimen and the objective optical system, it is possible to image the light-emitting site in the vicinity of the focal point from directions along a plurality of different optical axes to acquire a plurality of pieces of image information. It is thus possible to acquire a clear three-dimensional image.

In this case, the stage may be fixed and the rotation apparatus may rotate the objective optical system relative to the stage, or the objective optical system may be fixed and the rotation apparatus may rotate the stage relative to the objective optical system.

In the examination apparatus described above, the image-acquisition apparatus may include a deflecting member for directing the light emitted in a plurality of directions from the vicinity of the focal point inside the specimen to the objective optical system, which is disposed in one direction with respect to the specimen.

With this configuration, without moving the objective optical system which is disposed in one direction, or merely by translating it, it is possible to acquire an image formed by observing the vicinity of the focal point inside the specimen from a plurality of directions, and it is thus possible to more easily acquire a three-dimensional image.

The present invention provides an advantage in that it is possible to acquire a clear three-dimensional image of a light-emitting site inside a specimen.

DETAILED DESCRIPTION OF THE INVENTION

An examination apparatus according to an embodiment of the present invention is described below with reference to FIGS. 1 to 9.

Figure 1:
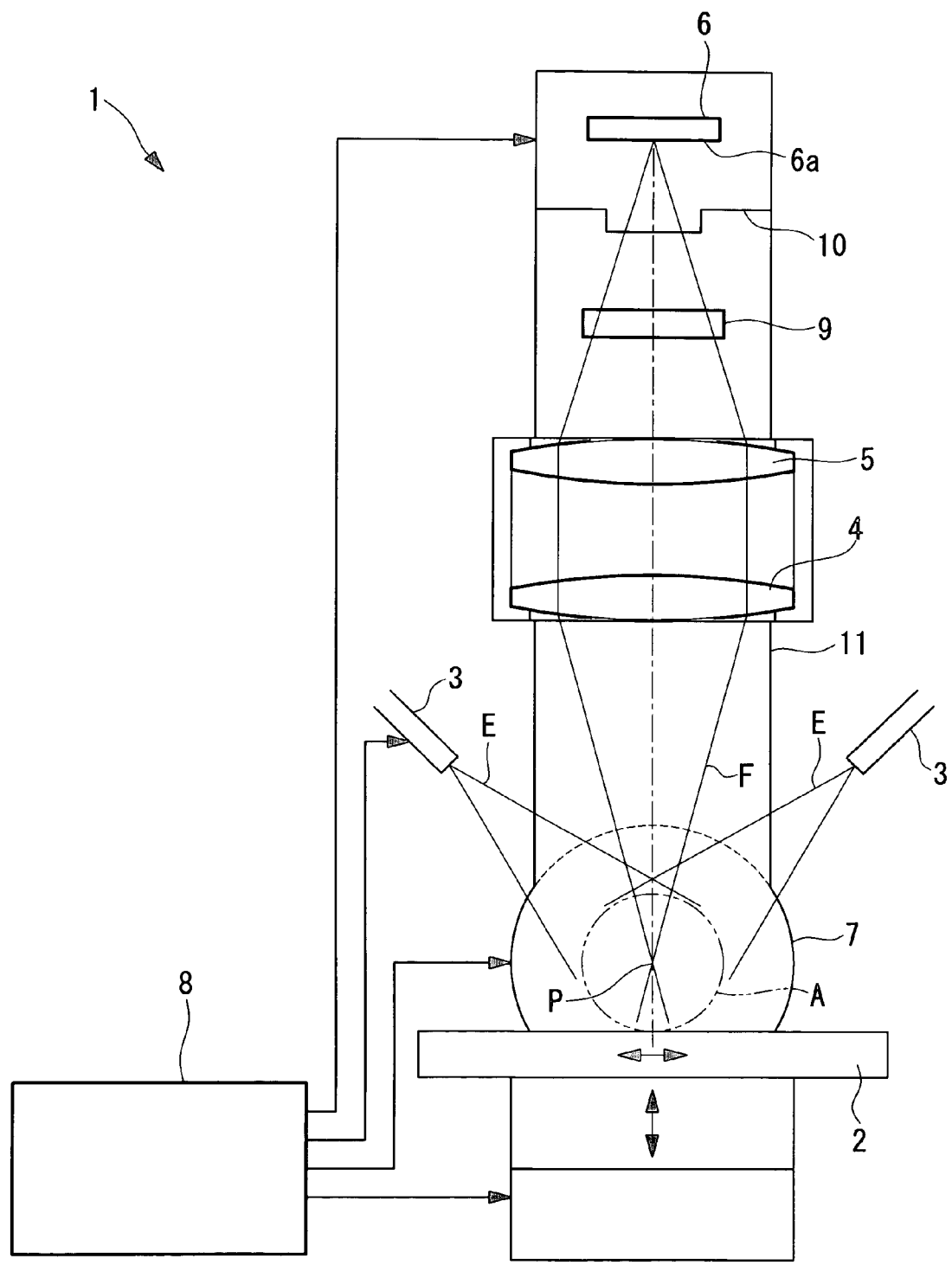
FIG. 1 is a diagram showing the overall configuration of an examination apparatus according to an embodiment of the present invention.

As shown in FIG. 1, an examination apparatus 1 according to this embodiment includes a stage 2 for mounting a specimen A such as a small laboratory animal like a mouse, into which a fluorescent substance is injected; an excitation light source 3 for irradiating the specimen A mounted on the stage 2 with excitation light E; an objective lens 4 for collecting fluorescence F which the fluorescent substance inside the specimen A generates when excited by the excitation light E emitted from the excitation light source 3; an image-forming lens 5 for imaging the fluorescence F collected by the objective lens 4; a image-acquisition device 6 for acquiring the fluorescence F imaged by the image-forming lens 5; a rotation apparatus 7 for rotating the objective lens 4, the image-forming lens 5, and the image-acquisition device 6 about a horizontal axis passing through the specimen A; and a control apparatus 8 for controlling the rotation apparatus 7, the stage 2, the excitation light source 3, and the image-acquisition device 6. Reference numeral 9 in this figure is an interference filter, which can be replaced by means of a turret (not shown in the drawing).

The stage 2 can move the specimen A mounted thereon, for example, up and down, as well as horizontally.

When the focal point of the objective lens 4 is located above the stage 2 and the specimen A is mounted on the stage 2, the focal point is located inside the specimen A.

The image-acquisition device 6 is, for example, a CCD provided in a digital camera 10, and an image-acquisition surface 6a thereof is disposed at a back focal plane of the image-forming lens 5. Accordingly, the fluorescence F emitted from the vicinity of a focal point P of the objective-lens 4 is imaged at the image-acquisition surface 6a of the image-acquisition device 6 by the image-forming lens 5 and is acquired by the image-acquisition device 6 as image information.

Figure 2:
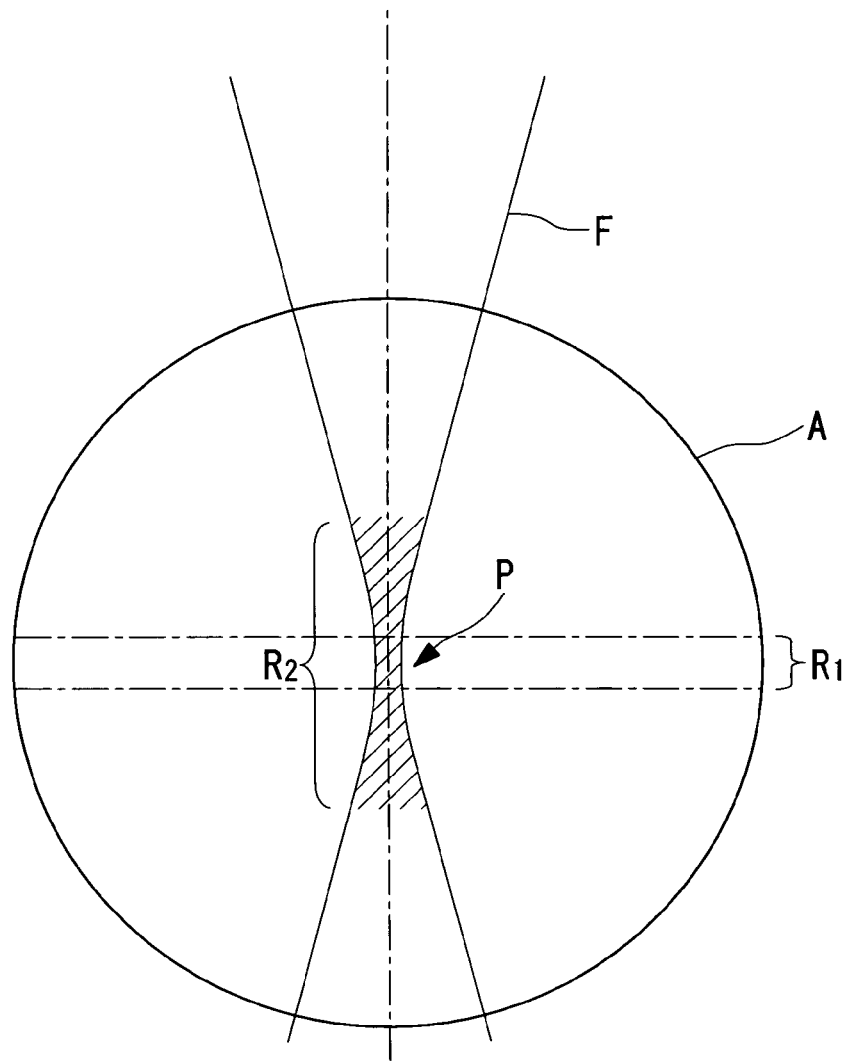
FIGS. 2 and 3 are illustrations for explaining fluorescence inside a specimen observed by the examination apparatus in FIG. 1.

In this case, although the fluorescence F emitted from the fluorescent substance is emitted in all directions, only the portion of the light emitted in a direction along the optical axis of the objective lens 4 is collected by the objective lens 4. In this case, as shown in FIG. 2, regarding the fluorescence F emitted from the focal point P disposed at an emission site inside the specimen A, the fluorescence F within a wide region, according to the numerical aperture of the objective lens 4, is collected by the objective lens 4.

Therefore, when acquired by the image-acquisition device 6, not only the fluorescence F from a focused region R1 in the vicinity of the focal point P, but also fluorescence F from a focused region R2 disposed at a position shifted in the optical-axis direction are simultaneously acquired. It is possible to construct a clear three-dimensional image based on a plurality of images obtained by acquiring only the fluorescence F from the focused region R1 in the vicinity of this focal point P while shifting the focal point P in the optical axis direction; however, because the images actually acquired also include the fluorescence F from the focus-shifted region R2, it is not possible to construct a clear three-dimensional image just by performing image acquisition while shifting the focal point P in the optical axis direction.

The rotation apparatus 7 includes a known motor and gear mechanism (not shown in the drawing). In response to command signals from the control apparatus 8, for example, the rotation apparatus 7 rotates an arm 11, to which the objective lens 4, the image-forming lens 5, and the image-acquisition device 6 are fixed, about a horizontal axis passing through the focal point P of the objective lens 4.

The control apparatus 8 drives the stage 2 and positions it so that the focal point P of the objective lens 4 is aligned with an examination site of the specimen A. Also, an image at each position is acquired by controlling the image-acquisition device 6 while driving the stage 2 to continuously move the specimen A in the optical-axis direction of the objective lens 4.

The control apparatus 8 also controls the rotation apparatus 7 to change the angle of the objective lens 4, the image-forming lens 5, and the image-acquisition device 6 with respect to the specimen A. Thus, by repeating the process described above at different angles, images formed by viewing the same examination site from a plurality of different directions are acquired by the image-acquisition device 6. The control apparatus 8 also constructs a three-dimensional image based on the plurality of pieces of image information obtained.

The method of constructing the three-dimensional image is, for example, the Radon transform method or the three-dimensional Fourier transform method.

Radon transformation and three-dimensional Fourier transformation are described, for example, in Susumu Kikuchi, et al., "Three-dimensional image reconstruction for biological micro-specimens using a double-axis fluorescence microscope", Optics Communications, vol. 138, issues 1-3, 15 May 1997, pp. 21-26 and Susumu Kikuchi, et al., "Three-dimensional microscopic computed tomography based on generalized Radon transform for optical imaging systems", Optics Communications, vol. 123, issues 4-6, 1 Feb. 1996, pp. 725-733.

The operation of the examination apparatus 1 according to this embodiment, having such a configuration, will be described below.

Figure 4:
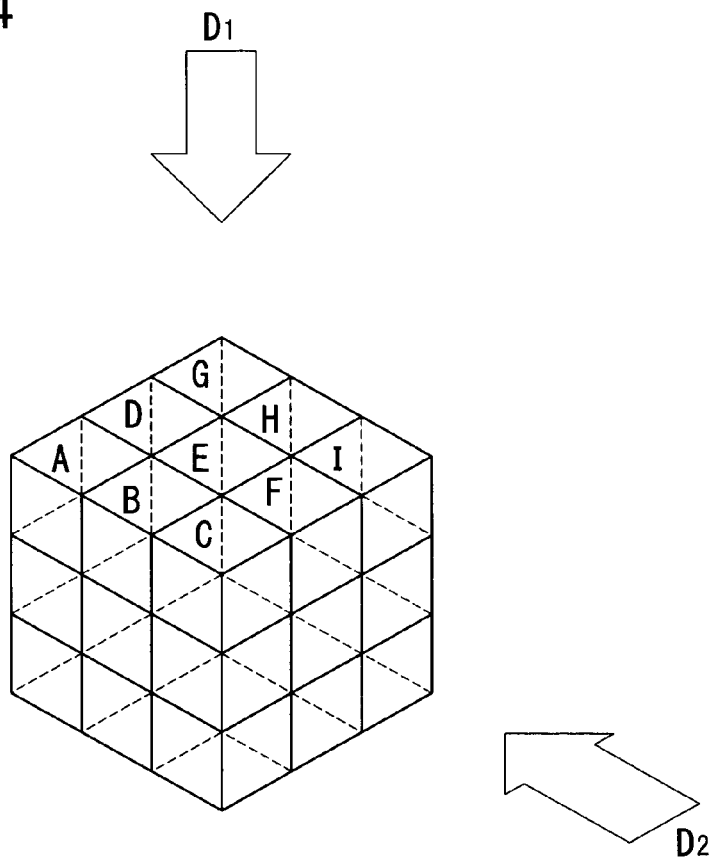
FIG. 4 is a diagram showing a model for explaining a three-dimensional image construction method used by the examination apparatus in FIG. 1.
Figure 5:
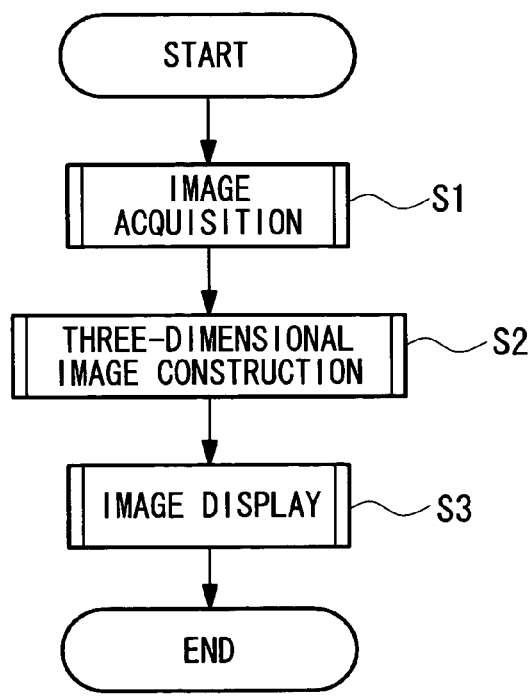
FIG. 5 is a flowchart for explaining the three-dimensional image-construction method in FIG. 4
Figure 6:
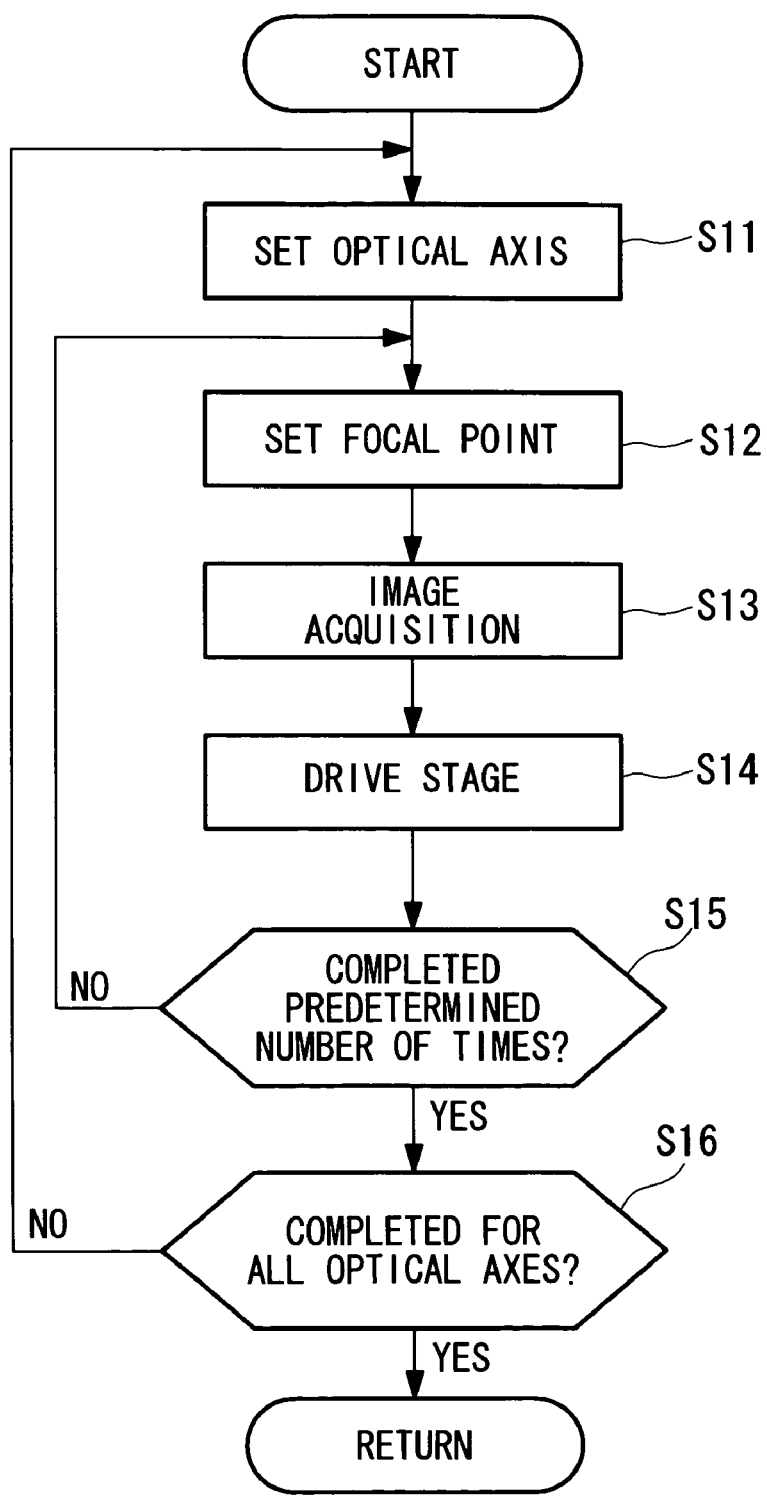
FIG. 6 is a flowchart for explaining the image-acquisition process of the flowchart in FIG. 5.
Figure 7:
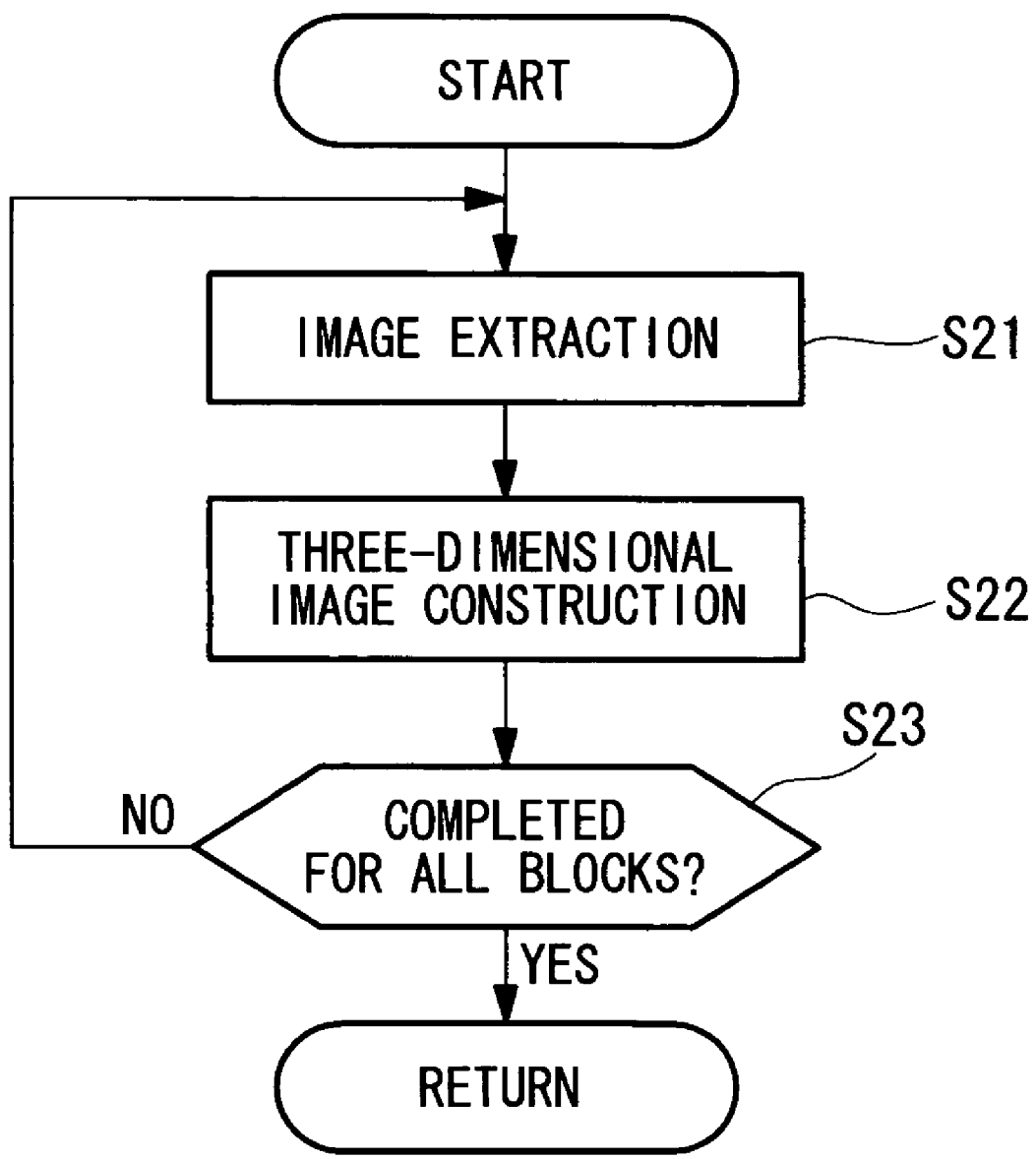
FIG. 7 is a flowchart for explaining the three-dimensional image-construction process of the flowchart in FIG. 5.

As shown in FIG. 4 for example, a method of constructing a three-dimensional image of an examination site inside the specimen A based on image information acquired from two directions, that is, the vertical direction D1 and the horizontal direction D2, with respect to the specimen A will be described here. FIGS. 5 to 7 are flowcharts of the three-dimensional image-construction method.

As shown in FIG. 5, to acquire a three-dimensional image, a plurality of pieces of image information are acquired (step S1), a three-dimensional image is constructed based on the plurality of pieces of image information acquired (step S2), and the constructed three-dimensional image is displayed (step S3).

As shown in FIG. 6, in the image-acquisition process (step S1), first, by operating the rotation apparatus 7, the objective lens 4, the image-forming lens 5, and the image-acquisition device 6 are rotated relative to the specimen A mounted on the stage 2 to position them so that the optical axes thereof are disposed in a first direction (vertical direction D1) (step S11). Next, by operating the stage 2, it is set so that the specimen A is moved in the optical-axis direction to locate the focal point P of the objective lens 4 at the examination site inside the specimen A (step S12).

In this state, the image-acquisition device 6 is operated to acquire an image of the examination site (step S13).

Then, the stage 2 is driven by a predetermined distance in the optical-axis direction (step S14), and the process for acquiring an image by the image-acquisition device 6 (step S13) is repeated a predetermined number of times (step S15). Accordingly, slice images of the vicinity of a plurality of focal points P separated by a predetermined distance in a first direction inside the specimen A are acquired.

Next, it is determined whether or not slice-image acquisition from all directions is completed (step S16). If it is completed, slice images are acquired in the second direction (horizontal direction D2) (steps S11 to S15). If slice-image acquisition from all directions is completed, flow proceeds to the three-dimensional image construction process (step S2 in FIG. 5).

As shown in FIG. 7, in the three-dimensional image construction process (step S2 in FIG. 5), image information acquired from different directions with respect to the same examination site in three-dimensional space is extracted (step S21 in FIG. 7) from image information of the plurality of slice images acquired in the image-acquisition process (step S1 in FIG. 5).

Then, based on the extracted image information, a three-dimensional image is constructed using three-dimensional Fourier transformation or the like (step S22).

Specifically, as shown in FIG. 4, the examination site is separated into a plurality of blocks in three-dimensional space. The image information acquired along the first direction D1 and the second direction D2 is sequentially extracted for each block A, B, . . . , and a three-dimensional image is constructed.

Then, it is determined whether or not three-dimensional image construction has been completed for all blocks A, B, . . . (step S23). If it is completed, flow proceeds to the three-dimensional image display process (step S3 in FIG. 5); if it is not completed, steps S21 and S22 above are repeated.

Figure 3:
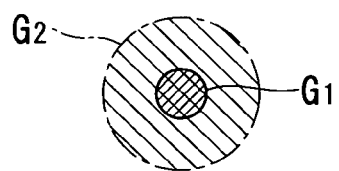

As described above, the image information acquired by each pixel of the image-acquisition device 6 is not limited to the thin region R1 in the vicinity of the focal point P of the objective lens 4; it also includes image information from the region R2, which is comparatively thick towards the front and rear in the optical-axis direction of that region, as shown in FIG. 2. Therefore, when the fluorescent substance exists in areas other than the vicinity of the focal point P, as shown in FIG. 3, in-focus image information G1 of the vicinity of the focal point P of the objective lens 4 and focus-shifted image information G2 of areas other than that area are superimposed and acquired.

Figure 8:
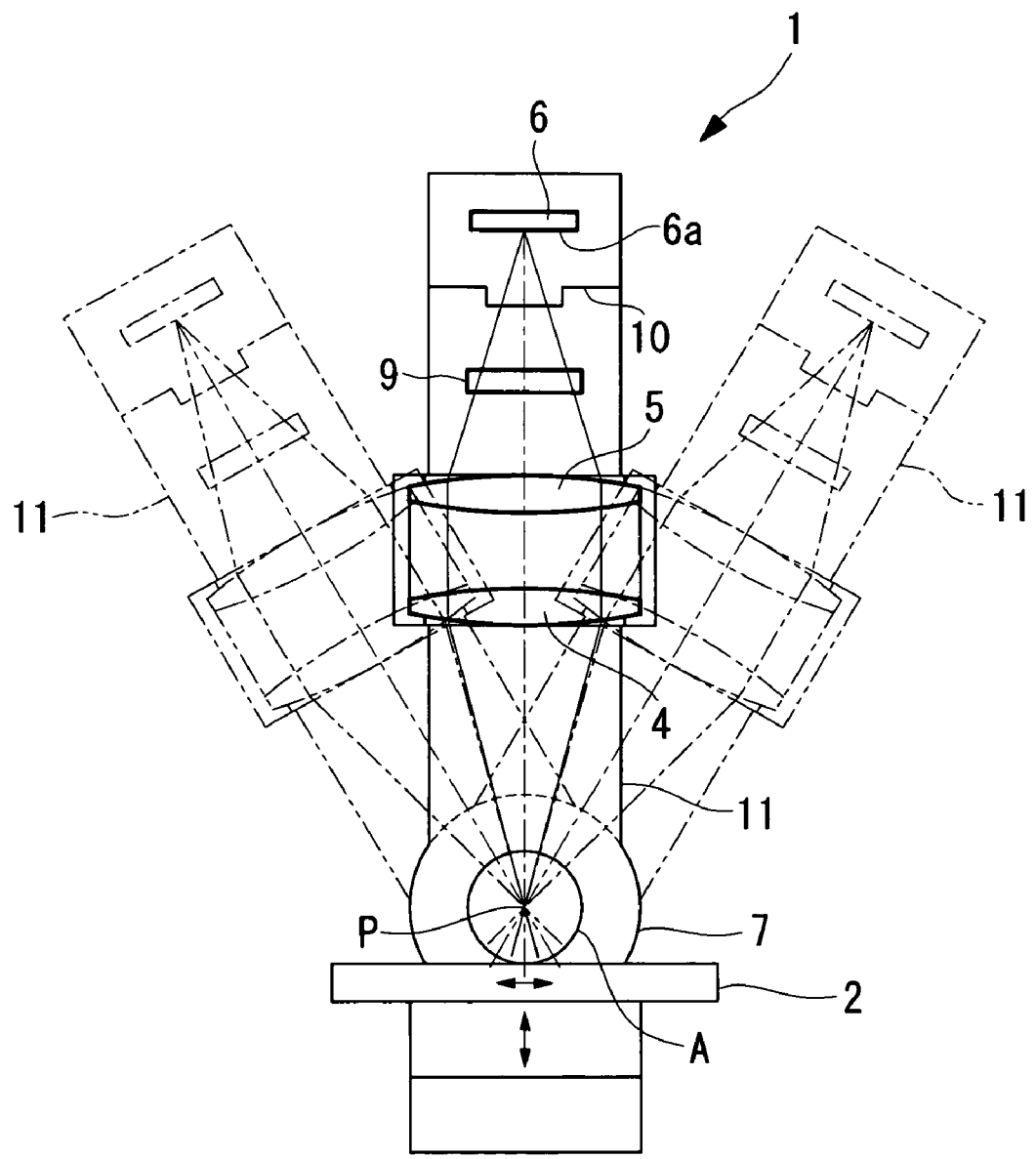
FIG. 8 is a diagram for explaining a case where the same specimen is observed from different optical-axis directions by the examination apparatus in FIG. 1.
Figure 9:
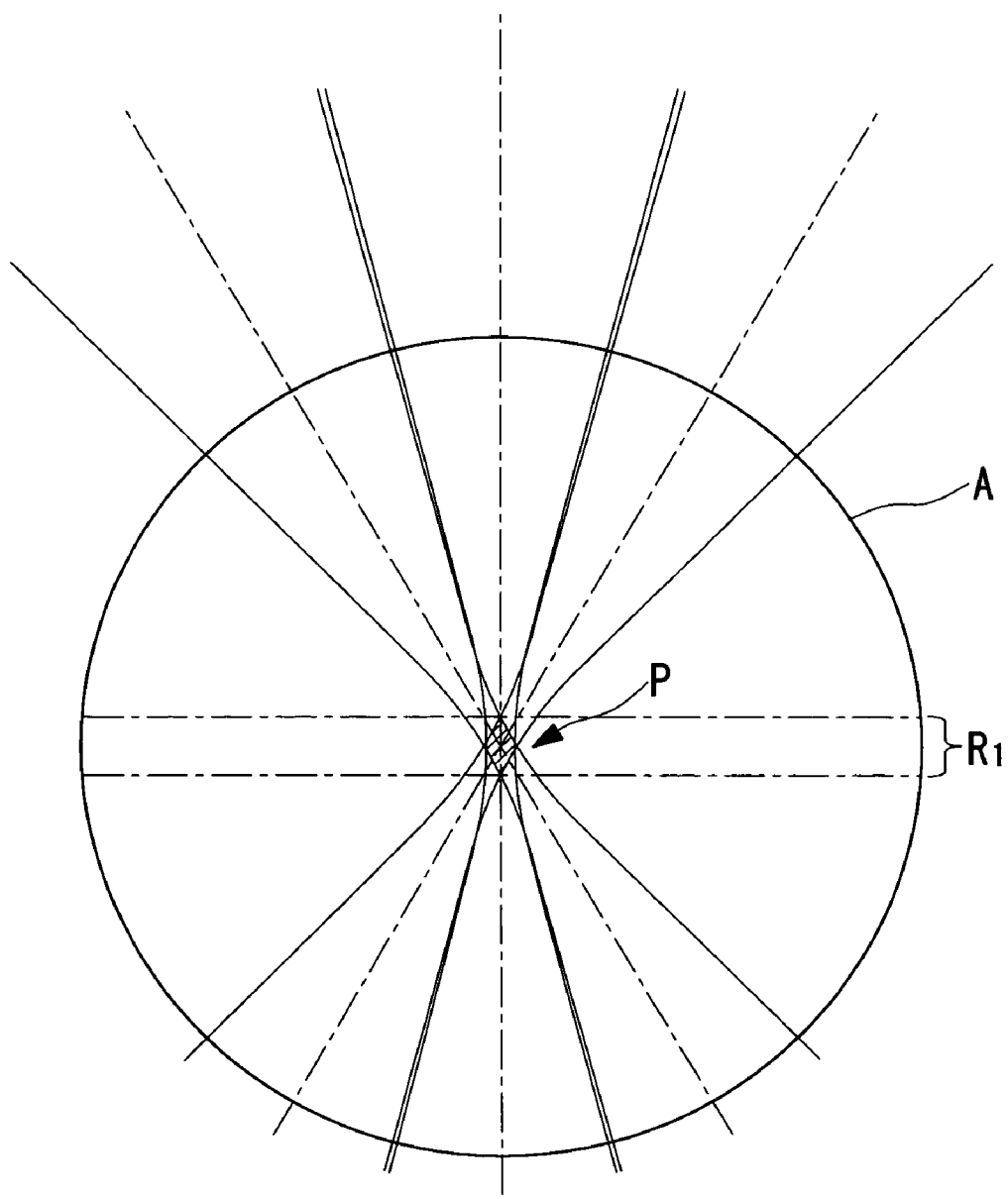
FIG. 9 is a diagram for explaining image information extracted using the examination shown in FIG. 8.

Then, as shown in FIG. 8, the rotation apparatus 7 is operated to rotate the arm 11 relative to the specimen A. By doing so, it is possible to acquire a plurality of pieces of image information from different optical-axis directions with respect to the same examination site. For example, by rotating the arm 11 by ±30° from the vertical direction, as shown in FIG. 8, it is possible to acquire image information of the same examination site from three different directions. Similarly to FIG. 3, each piece of image information also includes image information of areas other than the vicinity of the focal point P; however, as indicated by the oblique lines in FIG. 9, image information of comparatively narrow areas which intersect each other is included in these pieces of image information.

According to this embodiment, using the three-dimensional image construction method shown in the flowcharts in FIGS. 4 to 7, image information of narrow regions which intersect each other in the image information acquired from a plurality of directions is extracted at each point in the three-dimensional space of the examination site inside the specimen A. Therefore, it is possible to acquire a clear three-dimensional image.

Figure 10:
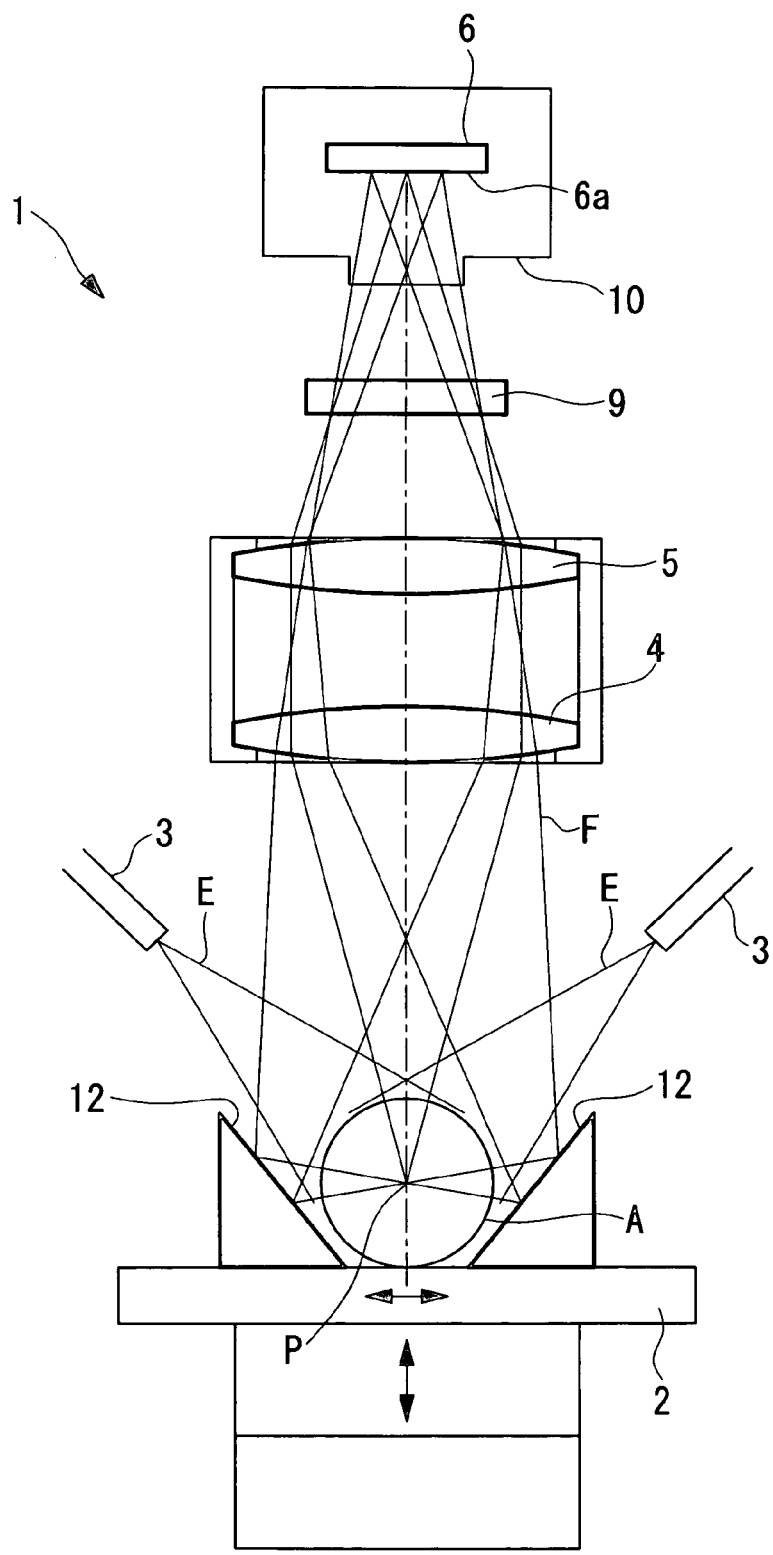
FIG. 10 is a diagram showing a first modification of the examination apparatus in FIG. 1.

In the examination apparatus 1 according to this embodiment, the viewing optical axis is disposed in a plurality of directions with respect to the specimen A by rotating the arm 11, to which the objective lens 4, the image-forming lens 5, and the image-acquisition device 6 are fixed, about a horizontal axis passing through the specimen A. Instead of this, however, a mirror 12 may be disposed at the side of the specimen A to deflect the fluorescence F emitted in the horizontal direction from the examination site towards the image-acquisition device 6. By doing so, it is possible to simultaneously acquire fluorescence images, formed by viewing the specimen A from three directions, using the same image-acquisition device 6, as shown in FIG. 10. By processing the image information obtained, it is possible to extract in-focus image information of the vicinity of the focal point P.

Figure 11:
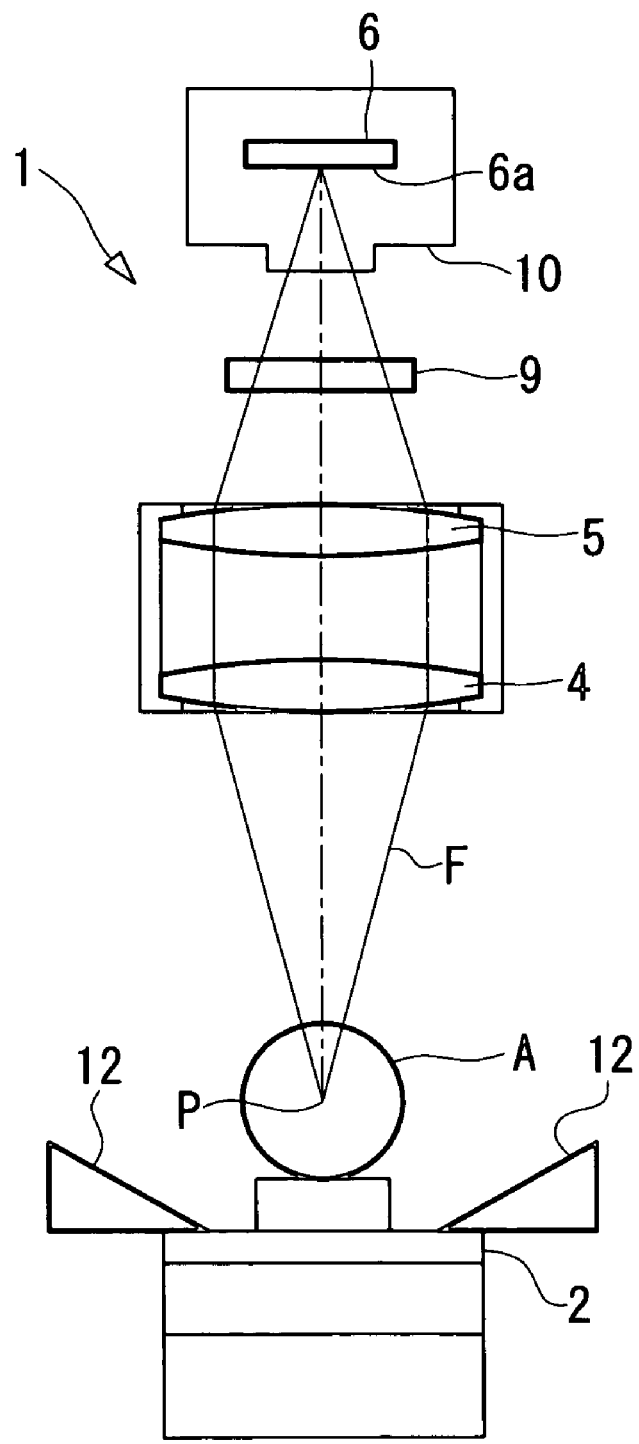
FIGS. 11 to 13 are diagrams showing a second modification of the examination apparatus in FIG. 1.
Figure 12:
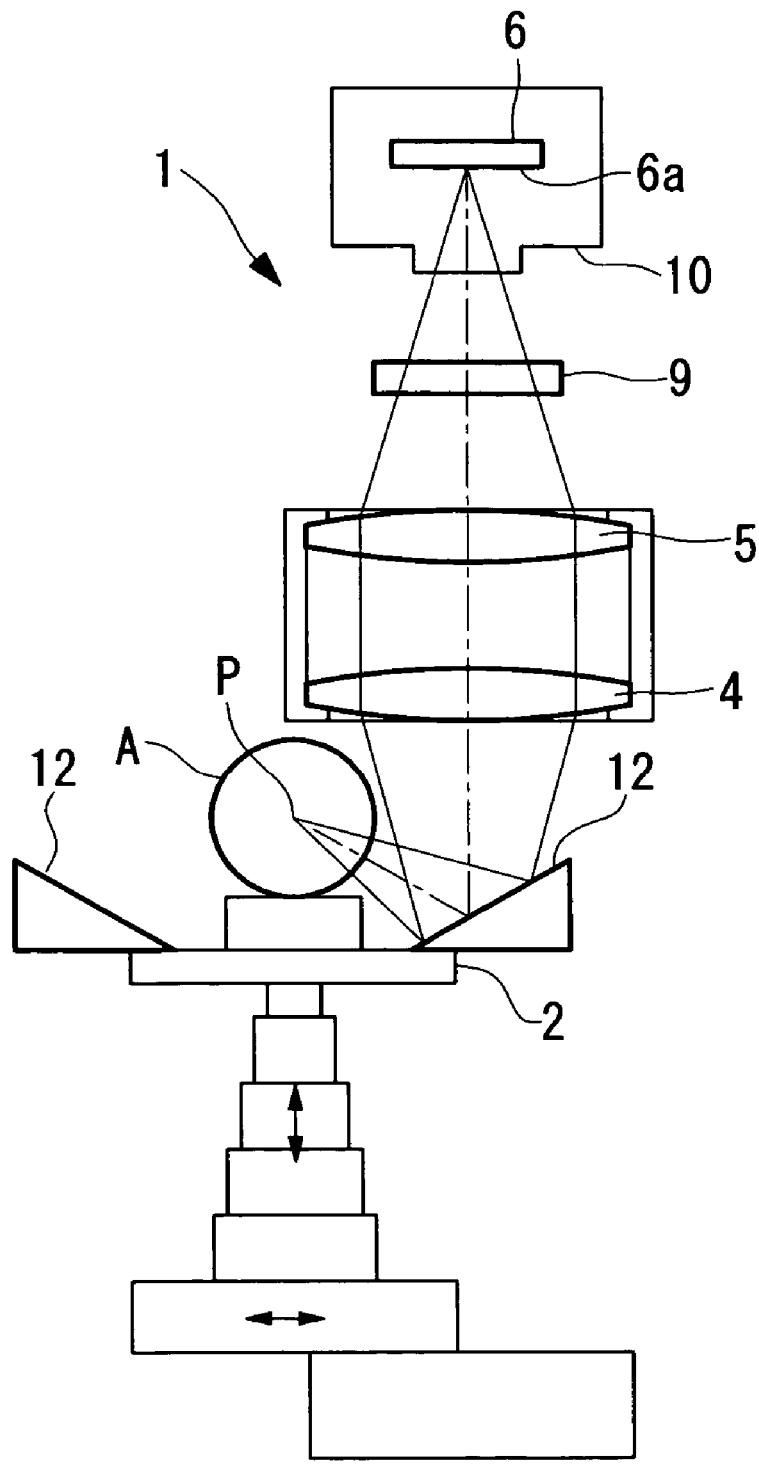
Figure 13:
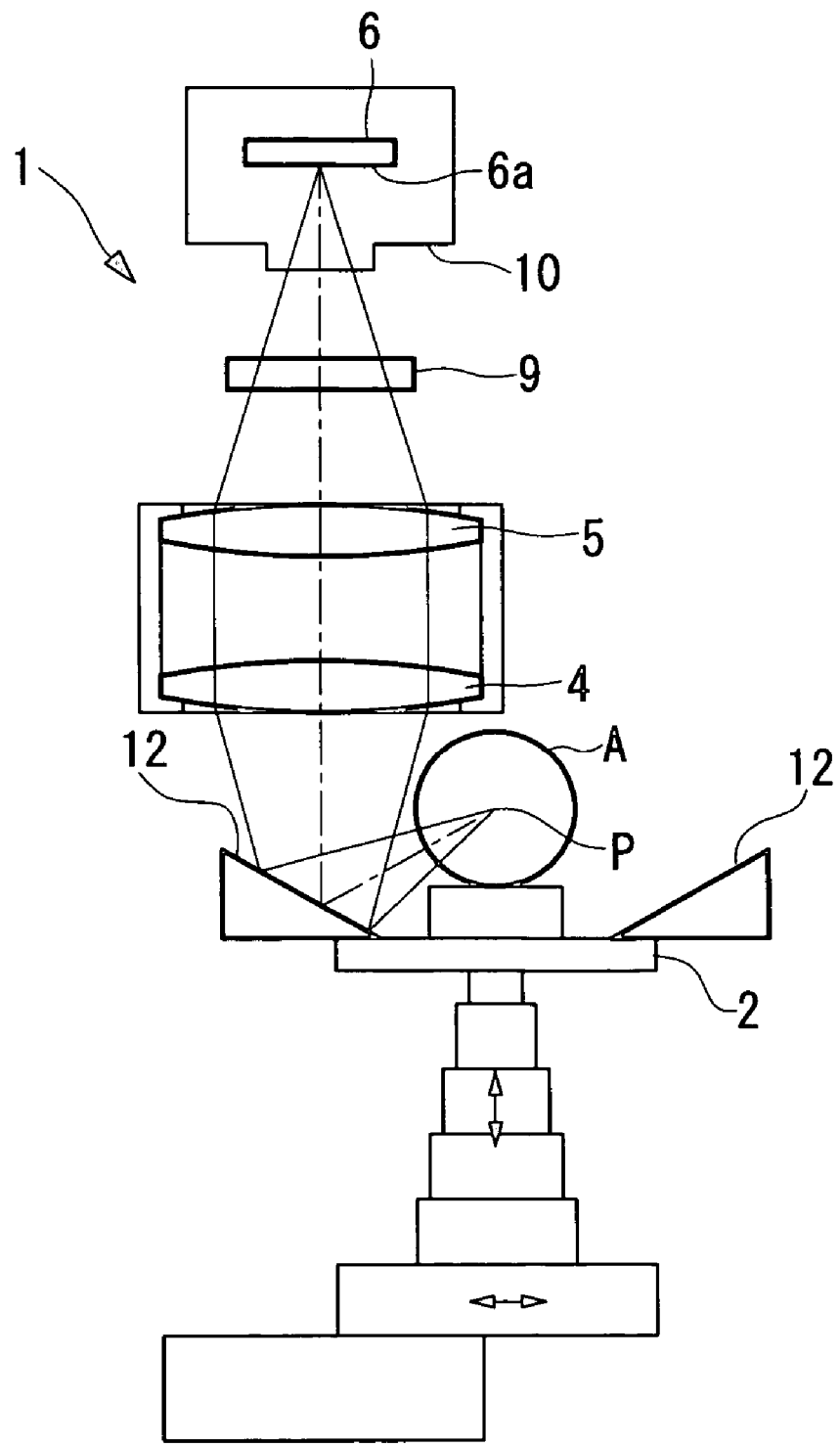

In addition, by driving the stage 2 to move the specimen A, it is possible to change to the state shown in FIG. 11, where the optical axis of the objective lens 4 is disposed in the vertical direction, and the states shown in FIG. 12 and 13, where the optical axis is deflected by the mirror 12 to be directed downward at an angle. The direction in which the optical axis is deflected by the mirror 12 is not limited to downward at an angle; it may be set to any other direction. Also, by using a plurality of mirrors 12, the light emitted vertically downward from the light-emitting site inside the specimen A may be deflected and collected by the objective lens 4.

Figure 14:
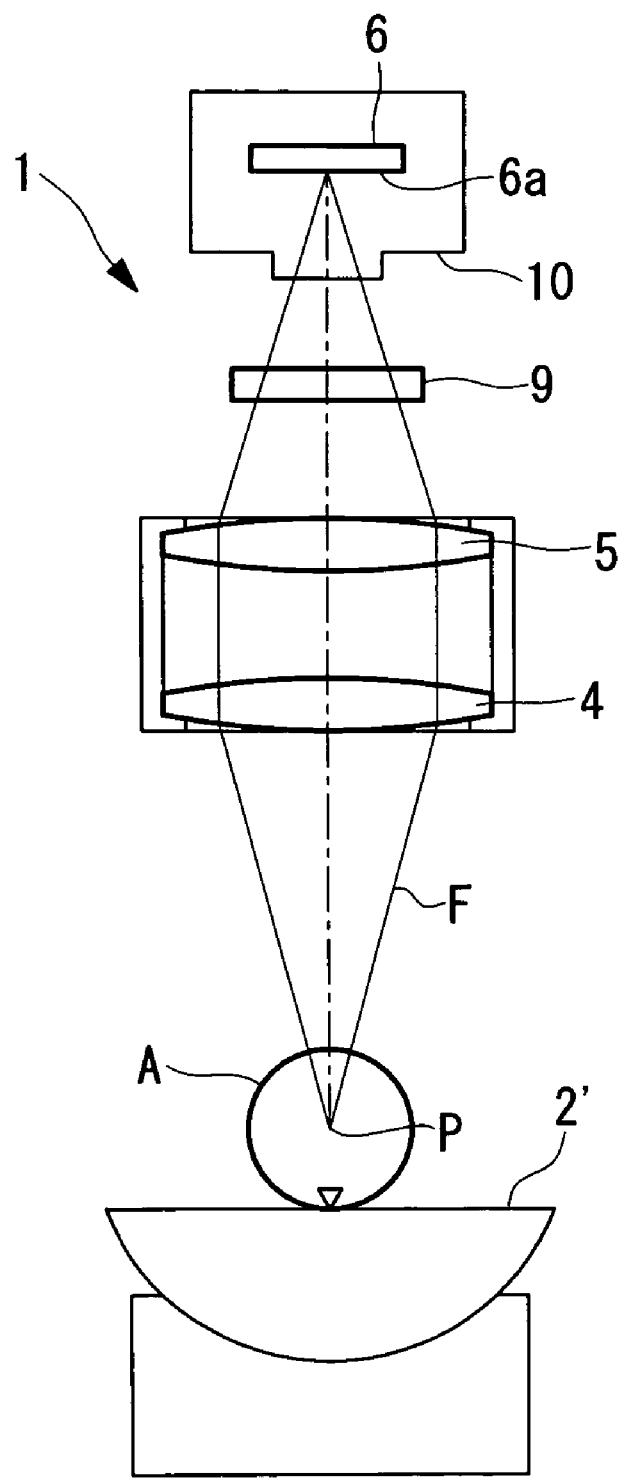
FIGS. 14 to 16 are diagrams showing a third modification of the examination apparatus in FIG. 1.
Figure 15:
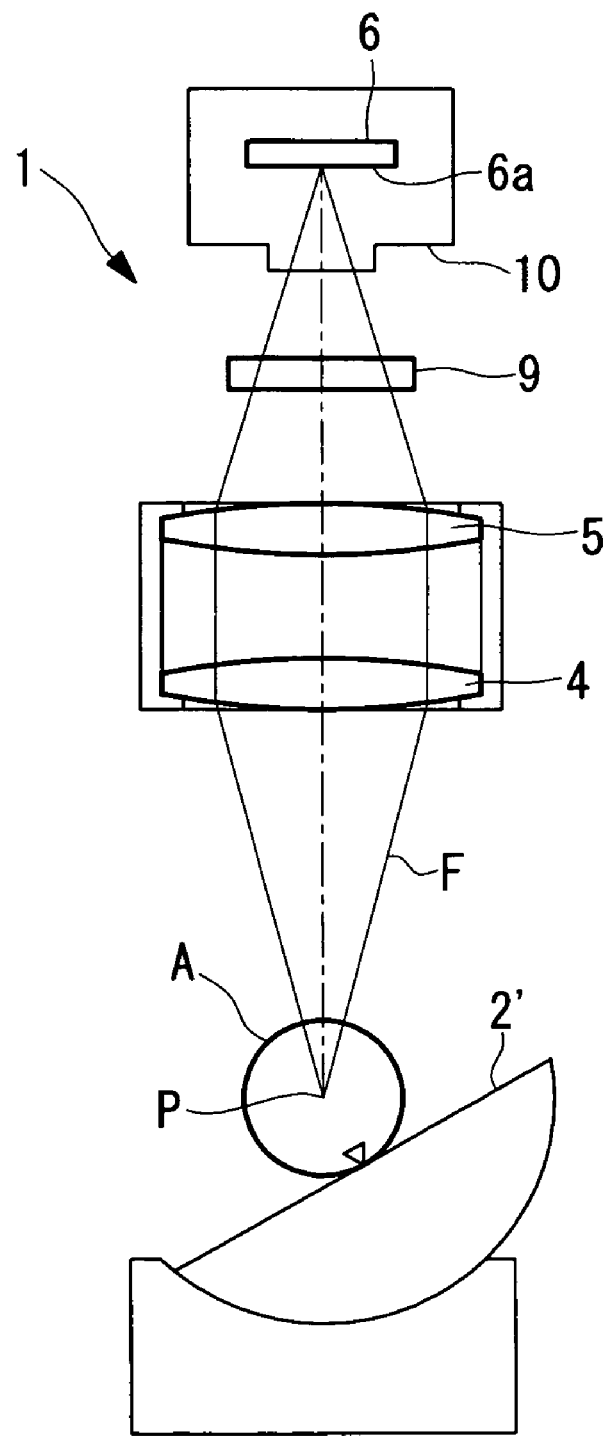
Figure 16:
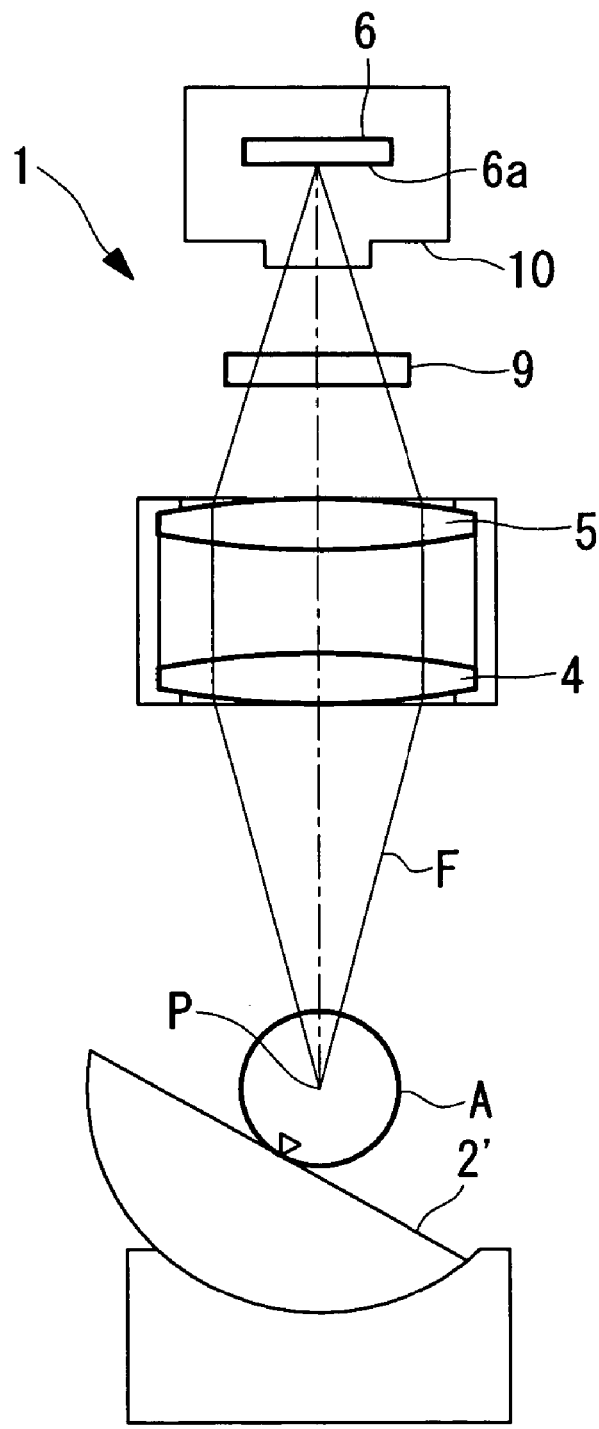

As shown in FIGS. 14 to 16, by tilting a stage 2', like a so-called gonio-stage, the specimen A may be tilted with respect to the optical axis.

Figure 17:
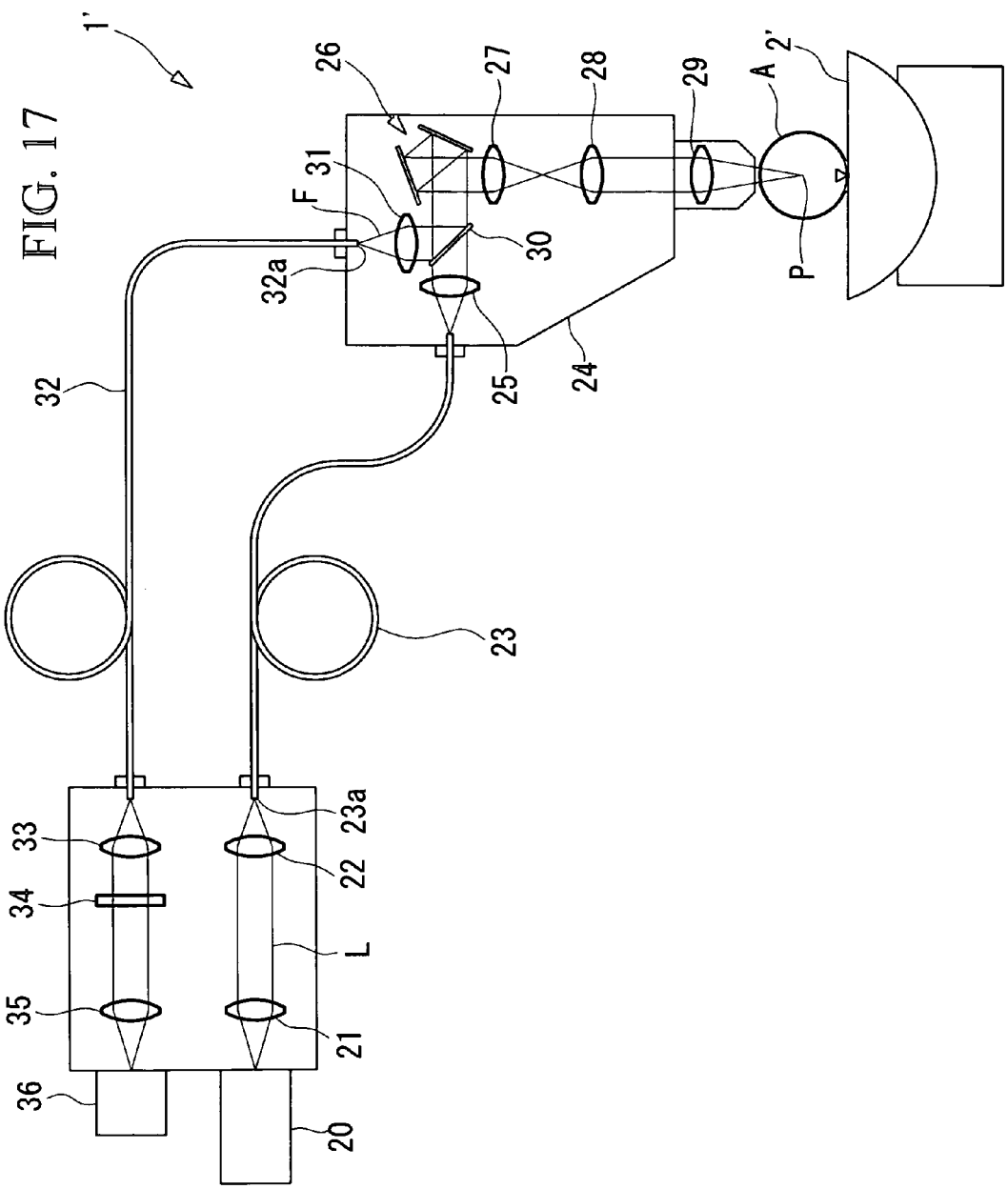
FIG. 17 is a diagram showing a fourth modification of the examination apparatus in FIG. 1.

This embodiment has been described in terms of an example in which the fluorescence F collected by the objective lens 4 is imaged with the image-acquisition 6 formed of the CCD; instead of this, however, as shown in FIG. 17, it may also be applied to an examination apparatus 1' of the scanning type.

In the examination apparatus 1' in FIG. 17, laser light emitted from a laser light source 20 and focused onto an end face 23a of an optical fiber 23 by coupling lenses 21 and 22 is guided to a microscope main body 24 by the optical fiber 23. The laser light guided to the microscope main body 24 is substantially collimated by a collimator lens 25. Thereafter, it is two-dimensionally scanned by a scanner 26, such as proximity galvanometer mirrors, and is relayed by a pupil-projection lens 27, and image-forming lens 28, and an objective lens 29 to irradiate a specimen A.

By irradiating the specimen A with the laser light L, a fluorescent substance inside the specimen A is excited and emits fluorescence F. The emitted fluorescence F is collected by the objective lens 29, returns via the image-forming lens 28, the pupil-projection lens 27, and the scanner 26, is split off from the laser light L by a dichroic mirror 30, and is focused onto an end face 32a of an optical fiber 32 by a coupling lens 32. The end face 32a of the optical fiber 32 effectively serves as a pinhole. The fluorescence F transmitted by the optical fiber 32 passes through a collimator lens 33, a barrier filter 34, and a focusing lens 35 and is detected by an optical detector 36, such as a photomultiplier tube.

In this case, because the end face 32a of the optical fiber 32 effectively functions as a pinhole, the fluorescence F reaching the optical detector 36 is restricted to fluorescence emitted from the vicinity of a focal point P of the objective lens 29; however, by increasing the core diameter of the optical fiber 32, the depth of field is increased, causing the same problem as that described above. As shown in FIG. 17, by changing the relative angle between the specimen A and the optical axis of the objective lens 29, the same site of the specimen A is observed from different optical-axis directions to acquire image information. Therefore, an advantage is afforded in that it is possible to acquire a clear three-dimensional image, similarly to the embodiments described above. It is possible to use any other method, apart from a gonio-stage 2', as the method of observing the same examination site from different optical-axis directions.

In the above description of this embodiment, the fluorescence F which the fluorescent substance inside the specimen A emits when radiated with excitation light from outside the specimen A is detected. Instead of this, however, it is possible to detect light emitted from an autofluorescent substance.

What is claimed is:

1. An examination apparatus comprising:
an objective optical system configured to position a focal point inside a specimen mounted on a stage, and to form images of a light-emitting site in a vicinity of the focal point inside the specimen from a plurality of different optical-axis directions by changing a relative angle to the stage;
an image-acquisition apparatus configured to detect each of the images, and to acquire a plurality of pieces of image information of the light-emitting site; and
a three-dimensional image forming unit configured to form a three-dimensional image of a light-emitting site in the vicinity of the focal point based on the plurality of pieces of image information acquired by the image-acquisition apparatus.

2. The examination apparatus according to claim 1, wherein the image-acquisition apparatus includes a rotation apparatus configured to relatively rotate the specimen and the objective optical system about an axis intersecting the optical axis in the vicinity of the focal point.

3. The examination apparatus according to claim 2, wherein the stage is fixed, and the rotation apparatus rotates the objective optical system relative to the stage.

4. The examination apparatus according to claim 2 wherein the objective optical system is fixed, and the rotation apparatus rotates the stage relative to the objective optical system.

5. The examination apparatus according to claim 1 wherein the image-acquisition apparatus includes a deflecting member configured to direct the light emitted in a plurality of directions from the vicinity of the focal point inside the specimen to the objective optical system, which is disposed in one direction with respect to the specimen.

* * * * *